United States Patent [19]

Audibert

[11] 4,225,605
[45] Sep. 30, 1980

[54] ERGOLENE OR ERGOLINE COMPOUNDS FOR TREATING CONGESTIVE HEART FAILURE

[75] Inventor: Alain Audibert, Basel, Switzerland

[73] Assignee: Sandoz Ltd., Basel, Switzerland

[21] Appl. No.: 970,349

[22] Filed: Dec. 18, 1978

[30] Foreign Application Priority Data

Dec. 22, 1977 [GB] United Kingdom ............... 53456/77

[51] Int. Cl.$^2$ .................... A61K 31/48; A61K 31/495
[52] U.S. Cl. ..................................... 424/250; 424/261
[58] Field of Search ................. 424/261, 250; 544/346

[56] References Cited

U.S. PATENT DOCUMENTS

| | | | |
|---|---|---|---|
| 3,732,231 | 5/1973 | Semonsky et al. | 424/261 |
| 3,752,814 | 8/1973 | Fluckiger et al. | 424/261 |
| 3,883,655 | 5/1975 | Fuxe | 424/261 |
| 3,944,582 | 3/1976 | Ferrari et al. | 424/261 |

OTHER PUBLICATIONS

Miller, "Proc. roy. Soc. Med.," vol. 70, (1977), pp. 16–24.

Primary Examiner—V. D. Turner
Attorney, Agent, or Firm—Gerald D. Sharkin; Robert S. Honor; Thomas O. McGovern

[57] ABSTRACT

A method for the treatment of congestive heart failure in animals comprises administering a therapeutically effective amount of an ergolene or ergoline having dopaminergic activity to an animal in need of such treatment.

13 Claims, No Drawings

ERGOLENE OR ERGOLINE COMPOUNDS FOR TREATING CONGESTIVE HEART FAILURE

The present invention relates to a new use of a compound chosen from ergolenes and ergolines possessing activity as dopaminergic stimulants, particularly peripheral dopaminergic stimulants as indicated by significant activity, e.g. a decrease in blood pressure and a selective vasodilation in mesenteric and renal blood vessels, in the anaesthetised dog (chloralose-urethane) on administration of from 5 to 25 μg/kg of the compound.

Alternatively such peripheral dopaminergic activity is indicated by central dopaminergic activity in standard tests e.g. those described in DOS No. 2,509,471.

The compound is, for example:
(a) 2-Bromo-α-ergocryptine (which is the preferred compound),
(b) 6-Methylergolin-8α-acetonitrile,
(c) 6-Methylergolin-8β-acetonitrile,
(d) 6-Methyl-2-chloro-ergoline-8β-acetonitrile,
(e) 6-Methyl-8α and β-(2-pyridylthiomethyl)ergolenes and ergolines, such as 6-methyl-8β-(2-pyridylthiomethyl)ergolene,
(f) 6-Methyl-8β-carbamoylmethylergoline,
(g) 6-Methyl-8α-(dimethylsulphamoylamino)ergoline,
(h) 6-Methyl-8α-(diethylsulphamoylamino)ergoline,
(i) 1,6-Dimethyl-8α-(dimethylsulphamoylamino)ergoline, or
(j) 6-methyl-8α-diethylcarbamoylamino-ergoline.

It has been found that the compounds are useful for the treatment of congestive heart failure, as indicated by standard trials. In one trial, four male patients, mean age 61 years, suffering from hypertension and arteriosclerotic cardiac insufficiency were studied. No diuretic or digitalis drugs had been administered for 15 days before the trial.

During the trial, the ratio PEP/LVET (PEP=pre-ejection period ; LVET=left-ventricular ejection time) before and 30, 60 and 90 minutes after administration of 2.5 to 5 mg of the compound was measured, and found to decrease significantly over the trial. Examples of the results obtained with 2-bromo-α-ergocryptine are as follows:

| | Ratio PEP/LVET | | |
|---|---|---|---|
| | Post-medication (minutes) | | |
| Pre-medication | 30 | 60 | 90 |
| 0.46 | 0.46 | 0.44 | 0.43 |

The cardiac frequency also remained stable.

For the abovementioned use, the dosage will, of course, vary depending on the mode of administration and therapy desired. However, in general, satisfactory results are obtained with a daily dosage of from about 0.01 to about 10 mg per kg animal body weight, conveniently given in divided doses 2 to 4 times a day or in sustained release form. For the larger mammal, the total daily dosage is in the range from about 2.5 to 40 mg, e.g. up to 10 mg, and dosage forms suitable for oral administration comprise from about 0.5 to about 20 mg of the compound admixed with a solid or liquid carrier or diluent.

The compound may be administered in pharmaceutically acceptable acid addition salt form. Such forms are known and have in general the same activity as the corresponding free base form. Examples of suitable acids for salt formation include methane-sulphonic acid, fumaric acid, tartaric acid and hydrochloric acid.

The compounds may be administered on their own or as a pharmaceutical composition. Such compositions are known and may be formulated in conventional manner to be, for example, tablets, powders, granules, capsules, suspensions, solutions, sirups and elixirs for enteral administration or injectable solutions and suspensions for parenteral administration.

The following Examples illustrate compositions suitable for use in the invention.

EXAMPLE 1: 2-Bromo-α-ergocryptine tablets

Tablets suitable for enteral administration and containing the following ingredients, may be produced in known manner.

| Ingredients | Weight | |
|---|---|---|
| 2-Bromo-α-ergocryptine methane-sulphonate | 2.87 mg | (corresponding to 2.5 mg of base) |
| Lactose | 96.18 mg | |
| Maize starch | 14.00 mg | |
| Polyvinylpyrrolidone | 5.00 mg | |
| Magnesium stearate | 0.70 mg | |
| Talc | 1.20 mg | |
| Colouring substances | 0.05 mg | |
| | 120 mg | |

EXAMPLE 2: 2-Bromo-α-ergocryptine capsules

Hard gelatine capsules suitable for enteral administration and containing the following ingredients, may be produced in known manner.

| Ingredients | Weight[1] | Weight[2] |
|---|---|---|
| 2-Bromo-α-ergocryptine methanesulphonate | 3.00 mg | 11.47 mg |
| Lactose | 105.00 mg | 160.03 mg |
| Maize starch | 20.00 mg | 120.00 mg |
| Talc | 4.50 mg | — |
| Aerosil ® 200 (Degussa) [colloidal silica] | 1.00 mg | 1.5 mg |
| Magnesium stearate | 1.50 mg | 3.0 mg |
| Maleic acid | — | 4.0 mg |
| Optionally colouring substances | q.s. | q.s. |
| | 135 mg | 300 mg |

[1]Corresponding to 2.61 mg of base
[2]Corresponding to 10 mg of base

EXAMPLES 3 and 4: Sterile suspension for injection and oral liquid suspension The following pharmaceutical compositions are formulated with the indicated amount of active agent using conventional techniques. The injectable suspension and the oral liquid suspension represent formulations useful as unit doses. The injectable suspension is suitable for administration once a day, whereas the oral liquid suspension is suitably administered 2 to 4 times per day for this purpose.

| Ingredient | Weight Sterile injectable suspension | Weight Oral liquid suspension |
|---|---|---|
| 2-bromo-α-ergocryptine | 7 mg | 7 mg |
| Sodium carboxy methyl cellulose, U.S.P. | 1.25 mg | 12.5 mg |
| Methyl cellulose | 0.4 mg | — |

-continued

| Ingredient | Weight Sterile injectable suspension | Weight Oral liquid suspension |
|---|---|---|
| Polyvinylpyrrolidone | 5 mg | — |
| Lecithin | 3 mg | — |
| Benzyl alcohol | 0.01 mg | — |
| Magnesium aluminum silicate | — | 47.5 mg |
| Flavor | — | q.s. |
| Color | — | q.s. |
| Methyl paraben, U.S.P. | — | 4.5 mg |
| Propyl paraben, U.S.P. | — | 1.0 mg |
| Polysorbate 80 (e.g. Tween 80) U.S.P. | — | 5 mg |
| Sorbitol solution, 70% U.S.P. | — | 2.500 mg |
| Buffer agent to adjust pH for desired stability | q.s. | q.s. |
| Water | (1) | (2) |

(1)for injection, q.s. to 1 ml.
(2)q.s. to 5 ml.

What we claim is:

1. A method for the treatment of congestive heart failure in mammals which comprises administering a therapeutically effective amount of an ergolene or ergoline having dopaminergic stimulant activity to an animal in need of such treatment.

2. A method according to claim 1 wherein the compound is 2-Bromo-α-ergocryptine.

3. A method according to claim 1 wherein the compound is 6-Methylergoline-8α-acetonitrile.

4. A method according to claim 1 wherein the compound is 6-Methylergoline-8β-acetonitrile.

5. A method according to claim 1 wherein the compound is 6-Methyl-2-chloro-ergoline-8α-acetonitrile.

6. A method according to claim 1 wherein the compound is 6-methyl-8β-(2-pyridylthiomethyl)ergolene.

7. A method according to claim 1 wherein the compound is 6-Methyl-8β-carbamoylmethylergoline.

8. A method according to claim 1 wherein the compound is 6-Methyl-8β-(dimethylsulphamoyl amino)ergoline.

9. A method according to claim 1 wherein the compound is 6-Methyl-8α-(diethylsulphamoylamino)ergoline.

10. A method according to claim 1 wherein the compound is 1,6-Diemethyl-8α-(dimethylsulphamoylamino)ergoline.

11. A method according to claim 1 wherein the compound is 6-methyl-8α-diethylcarbamoylamino ergoline.

12. A method according to claim 1 in which 2.5 to 40 milligrams of the ergolene or ergoline is administered daily.

13. A method according to claim 1 in which 0.5 to 20 milligrams of the ergolene or ergoline is administered orally per unit dose.

* * * * *